(12) United States Patent
Stern et al.

(10) Patent No.: US 8,853,220 B1
(45) Date of Patent: Oct. 7, 2014

(54) SYNTHESIS OF 2,6,9-TRI-SUBSTITUTED-4,8-DINITRO-2,6,9-TRIAZABICYCLO[3.3.1]NONA-3,7-DIENE INTERMEDIATES TOWARD THE PREPARATION OF POLYAZA-ADAMANTANES

(75) Inventors: Alfred G. Stern, Upper Marlboro, MD (US); Craig J. Diamond, Bryans Road, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 183 days.

(21) Appl. No.: 12/932,929

(22) Filed: Feb. 25, 2011

(51) Int. Cl.
*C07D 487/08* (2006.01)
*C07D 487/18* (2006.01)

(52) U.S. Cl.
CPC ............ *C07D 487/18* (2013.01); *C07D 487/08* (2013.01)
USPC ......... 514/259.4; 544/279; 544/251; 514/267

(58) Field of Classification Search
CPC .................................................... C07D 487/08
USPC ................ 544/279; 514/259.4, 259.41, 259.1
See application file for complete search history.

(56) References Cited

U.S. PATENT DOCUMENTS 7,432,331 B2    10/2008    Kozlowski et al.

OTHER PUBLICATIONS

Ostercamp et al. (Journal of Heterocyclic Chemistry, 2000, 37(5), pp. 1357-1359).*

* cited by examiner

*Primary Examiner* — Susanna Moore
(74) *Attorney, Agent, or Firm* — Fredric J. Zimmerman

(57) ABSTRACT

The present invention relates to methods for synthesizing energetic compounds and intermediates thereof. Specifically, the present invention relates to methods for synthesizing adamantanes and intermediates that are useful in such synthesis. Synthesized intermediates are useful in the synthesis of bicyclic and tricyclic substituted adamantanes. Examples of various intermediates are: acyclic 2-nitromalonaldehyde intermediates, 2,6,9-tri-substituted-4,8-dinitro-2,6,9-triazabicyclo[3.3.1]nona-3,7-dienes and 2,6-dinitro-4,8,9,10-tetra-aza-4,8,9,10-tetra-substituted adamantanes. Intermediates synthesized according to the methods of the present invention are useful toward the synthesis of tetraaza-adamantanes, which can serve as precursors to potentially superior new high-energy-density compounds (HEDCs). The tricyclic intermediate compound has a structure of Formula III:

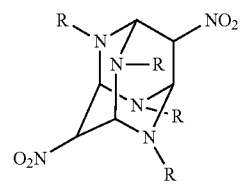

where R is one of a benzyl, 4-methoxybenzyl, acetyl, nitro, formyl, allyl, and a carboethoxyl group.

14 Claims, No Drawings

SYNTHESIS OF 2,6,9-TRI-SUBSTITUTED-4,8-DINITRO-2,6,9-TRIAZABICYCLO[3.3.1]NONA-3,7-DIENE INTERMEDIATES TOWARD THE PREPARATION OF POLYAZA-ADAMANTANES

STATEMENT OF GOVERNMENT INTEREST

The invention described herein may be manufactured and used by or for the Government of the United States of America for governmental purposes without the payment of any royalties thereon or therefore.

FIELD OF INVENTION

The present invention relates to methods for synthesizing energetic compounds and intermediates thereof. Specifically, the present invention relates to methods for synthesizing adamantanes and intermediates that are useful in such synthesis.

BACKGROUND OF THE INVENTION

Organic explosives typically consist of a carbon core and incorporate covalently bonded oxidizer groups such as nitro, nitramine, etc. N—N and N—O bonds contained in such compounds can contribute to a positive heat of formation.

Adamantanes are $C_{10}H_{16}$ alicyclic hydrocarbons whose structure has the same arrangement of carbon atoms as does the basic unit of the diamond lattice. Adamantane was first synthesized in 1941 by V. Prelog from Meerwein's ester. Adamantanes have highly rigid skeletons with cores that exhibit very little strain and thus exhibit high thermal stability. However, steric considerations have hampered the synthesis of stable, more energetic substituted adamantanes.

Accordingly, there is a need for intermediates and synthetic methods for making substituted adamantanes. Specifically, synthetic methods that enable substitution of some of the framework carbon atoms by nitrogen atoms are important because adjusting the carbon and nitrogen atom counts may be desirable for attaining optimum explosive properties.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In one embodiment, a bicyclic intermediate compound is described having the structure of Formula II:

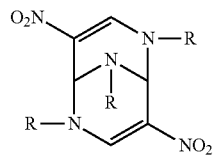

wherein each R represents any suitable organic moiety that does not render the compound unstable; or a pharmaceutically acceptable salt or solvate thereof.

In various embodiments, the bicyclic intermediate compound may be any of the following representative compounds: 2,6,9-Tribenzyl-4,8-dinitro-2,6,9-triazabicyclo[3.3.1]nona-3,7-diene; 2,6,9-Tri(4-methoxybenzyl)-4,8-dinitro-2,6,9-triazabicyclo[3.3.1]nona-3,7-diene; 2,6,9-Triacetyl-4,8-dinitro-2,6,9-triaza-bicyclo[3.3.1]nona-3,7-diene; 2,4,6,8,9-Pentanitro-2,6,9-triaza-bicyclo[3.3.1]nona-3,7-diene; 2,6,9-Triformyl-4,8-dinitro-2,6,9-triaza-bicyclo[3.3.1]nona-3,7-diene; 2,6,9-Triallyl-4,8-dinitro-2,6,9-triaza-bicyclo[3.3.1]nona-3,7-diene; 2,6,9-Tricarboethoxyl-4,8-dinitro-2,6,9-triaza-bicyclo[3.3.1]nona-3,7-diene; or a pharmaceutically acceptable salt or solvate thereof.

In another embodiment, a method is described for preparing a bicyclic intermediate compound comprising reacting sodium nitromalonaldehyde monohydrate with a substituted amine to form at least one bicyclic intermediate. In further embodiments, the substituted amine is a primary alkylamine or primary arylamine. Alternatively, the substituted amine can be benzylamine or allylamine.

In an alternative embodiment, a method is described for preparing a bicyclic intermediate compound comprising reacting an acyclic intermediate compound having a structure of Formula I:

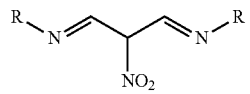

with a mono-substituted acyclic intermediate compound having a structure of Formula I':

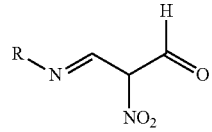

to form at least one bicyclic intermediate. In further embodiments, the substituted amine is a primary alkylamine or primary arylamine. Alternatively, the substituted amine can be benzylamine or allylamine.

Other aspects of the invention are found throughout the specification.

DETAILED DESCRIPTION OF THE INVENTION

The present invention relates to methods for synthesizing energetic compounds and intermediates thereof. Specifically, the present invention relates to methods for synthesizing adamantanes and intermediates that are useful in such synthesis.

When the terms "one," "a," or "an" are used in this disclosure, they mean "at least one" or "one or more," unless otherwise indicated.

The disclosure that follows will refer generally to three types of generic structures as follows:

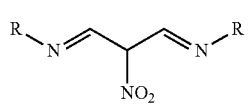

Formula I

Formula I represents the structure of acyclic 2-nitromalonaldehyde intermediates that are useful in the synthesis of bicyclic compounds, which in turn are useful as intermediates in the synthesis of tricyclic substituted adamantanes. As used herein, the term "acyclic" refers to the core structure, and not to the R group, which may or may not be acyclic.

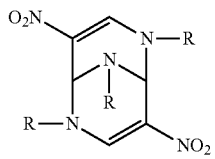

Formula II

Formula II represents the structure of the bicyclic compounds: 2,6,9-tri-substituted-4,8-dinitro-2,6,9-triazabicyclo[3.3.1]nona-3,7-dienes. As stated above, such compounds are useful as intermediates in the synthesis of tricyclic substituted adamantanes.

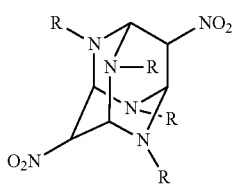

Formula III

Formula III represents the structure of the tricyclic substituted adamantanes: 2,6-dinitro-4,8,9,10-tetraaza-4,8,9,10-tetra-substituted adamantanes.

Acyclic Intermediates

The acyclic intermediates according to Formula I are synthesized, for example, from sodium nitromalonaldehyde monohydrate and an appropriate substituted amine, in an exemplary embodiment, containing a group removable later by chemical means, such as benzylamine or allylamine.

The acid-catalyzed condensation of sodium nitromalonaldehyde monohydrate with primary alkylamines and primary arylamines generally occurs stepwise, to form nitroenamines as products also containing an imine or Schiff base functionality. In the first step of the condensation, the amine and aldehyde give rise to an aminal, which is dehydrated under acidic conditions to afford the corresponding Schiff base (imine). Depending upon the nature of the primary amine, the reaction solvent(s) and the acidity strength of the catalyst (e.g. formic acid), the acyclic compounds represented by Formula I can be formed as the major products.

In the practice of the present invention, R may be any suitable organic moiety that does not render the compound unstable. Exemplary R groups include, for example, the following: benzyl, alkoxybenzyl, acetyl, nitro, formyl, allyl and carboalkoxyl.

The following compounds are representative acyclic intermediates:

Acyclic Intermediate 1 (I1): Bis(N-benzylimino)-2-nitromalonaldehyde (CAS Name: Benzenemethanamine, N-[2-nitro-3-[(phenylmethyl)amino]-2-propen-1-ylidene]-)

Acyclic Intermediate 2 (I2): Bis[N-(4-methoxybenzylimine)] of 2-nitromalonaldehyde (CAS Name: (4-Methoxyphenyl)methanamine, N-[2-nitro-3-[(4-methoxyphenylmethyl)amino]-2-propen-1-ylidene]-)

Acyclic Intermediate 3 (I3): Bis(N-acetylimine) of 2-nitromalonaldehyde (CAS Name: Acetamide, N-[2-nitro-3-[(acetyl)amino]-2-propen-1-ylidene]-)

Acyclic Intermediate 4 (I4): Bis(N-nitroimine) of 2-nitromalonaldehyde

Acyclic Intermediate 5 (I5) Bis(N-formylimine) of 2-nitromalonaldehyde (CAS Name: Formamide, N-[2-nitro-3-[(formyl)amino]-2-propen-1-ylidene]-)

Acyclic Intermediate 6 (I6): Bis(N-allylimine) of 2-nitromalonaldehyde

Acyclic Intermediate 7 (I7): Bis(N-carboethoxylimine) of 2-nitromalonaldehyde

Bicyclic Compounds

The acyclic intermediates just described are useful in the synthesis of bicyclic compounds (BCs) that are useful as intermediates in the synthesis of tricyclic compounds (TCs). Depending upon the nature of the primary amine, the reaction solvent(s) and the acidity strength of the catalyst (e.g. formic acid), the bicyclic compounds represented by Formula II can be formed as the major products and under certain reaction conditions, the tricyclic compounds represented by Formula III can be detected in the crude reaction mixture. Synthesis of the bicyclic compounds generally involves reacting sodium nitromalonaldehyde monohydrate with the appropriate substituted amine or by reaction of the acyclic intermediate represented by Formula I with the appropriate substituted amine as described in greater detail in the Examples section. Reaction conditions can be determined using routine optimization.

The following compounds are representative bicyclic intermediates:

Bicyclic Intermediate 1 (BC1): 2,6,9-Tribenzyl-4,8-dinitro-2,6,9-triazabicyclo[3.3.1]nona-3,7-diene Bicyclic Intermediate 2 (BC2): 2,6,9-Tri(4-methoxybenzyl)-4,8-dinitro-2,6,9-triazabicyclo[3.3.1]nona-3,7-diene Bicyclic Intermediate 3 (BC3): 2,6,9-Triacetyl-4,8-dinitro-2,6,9-triaza-bicyclo[3.3.1]nona-3,7-diene Bicyclic Intermediate 4 (BC4): 2,4,6,8,9-Pentanitro-2,6,9-triaza-bicyclo[3.3.1]nona-3,7-diene Bicyclic Intermediate 5 (BC5): 2,6,9-Triformyl-4,8-dinitro-2,6,9-triaza-bicyclo[3.3.1]nona-3,7-diene Bicyclic Intermediate 6 (BC6): 2,6,9-Triallyl-4,8-dinitro-2,6,9-triaza-bicyclo[3.3.1]nona-3,7-diene Bicyclic Intermediate 7 (BC7): 2,6,9-Tricarboethoxyl-4,8-dinitro-2,6,9-triaza-bicyclo[3.3.1]nona-3,7-diene Tricyclic Compounds Again, depending upon the nature of the primary amine, the reaction solvent(s) and the acidity strength of the catalyst (e.g. formic acid), the bicyclic compounds represented by Formula II can be formed as the major products and under certain reaction conditions, the tricyclic compounds represented by Formula III can be detected in the crude reaction mixture.

The following compounds are representative tricyclic compounds:

Tricyclic Compound 1 (TC1): 2,6-dinitro-4,8,9,10-tetraaza-4,8,9,10-tetrabenzyl-adamantane Tricyclic Compound 2 (TC2): 2,6-dinitro-4,8,9,10-tetraaza-4,8,9,10-tetra(4-methoxybenzyl)-adamantane (also may be referred to as "4-MeOBn-TC")

Tricyclic Compound 3 (TC3): 2,6-dinitro-4,8,9,10-tetraaza-4,8,9,10-tetraacetyl-adamantane (also may be referred to as "Ac-TC")

Tricyclic Compound 4 (TC4): 2,4,6,8,9,10-hexanitro-4,8,9,10-tetraaza-adamantane (also may be referred to as "$NO_2$-TC")

Tricyclic Compound 5 (TC5): 2,6-dinitro-4,8,9,10-tetraaza-4,8,9,10-tetraformyl-adamantane (also may be referred to as "HCO-TC")

Tricyclic Compound 6 (TC6): 2,6-dinitro-4,8,9,10-tetraaza-4,8,9,10-tetraallyl-adamantane (also may be referred to as "Allyl-TC")

Tricyclic Compound 7 (TC7): 2,6-dinitro-4,8,9,10-tetraaza-4,8,9,10-tetracarboethoxyl-adamantane (also may be referred to as "EtOCO-TC")

Uses

The intermediates disclosed above are useful toward the synthesis of tetraaza-adamantanes, which can serve as precursors to superior new high-energy-density compounds (HEDCs), also referred to as "organic cage compounds", such as polynitrotetraaza-adamantanes. These compounds have superior energetic properties, due to their higher calculated densities and high calculated performance parameters (e.g. detonation properties).

The tetraazaadamantanes disclosed above are expected to be key precursors which, after protecting group removal by either hydrogenolysis, nitrolysis or other chemical means, and subsequent polynitration could afford novel, high-performance HEDCs including hexanitro- and octanitro-tetraazaadamantanes, and may provide potential pharmaceutical uses and benefits.

EXAMPLES

Actual

Methods for synthesizing representative intermediates are described in this section. All intermediates described herein but not specifically mentioned below, can be synthesized by varying the below methods using well known organic chemical synthesis techniques.

Example 1

Compound I1

Compound I1 can be represented by Formula IV as follows:

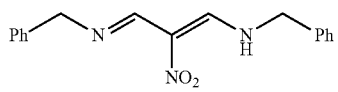

Formula IV for Compound I1

As depicted, "Ph" is an unsubstituted phenyl moiety.

Synthesis of (3E)-N-((E)-3-(benzylimino)-2-nitropropylidene)(phenyl)methanamine (Compound I1)

A turbid, yellow-orange solution of sodium nitromalonaldehyde monohydrate (15.7 mg, 0.10 mmol) in DMF (275 uL) and water (25 uL) was added dropwise over a 2 min period to a solution of benzylamine (27.4 uL, 0.25 mmol) in DMF (165 uL), water (15 uL) and 96% formic acid (0.94 uL, 0.025 mmol) and was stirred at room-temperature for 24 h. A few drops of the reaction mixture were added to ~1 mL water giving a white, opaque emulsion that was extracted with EtOAc twice. The combined organics were dried over $Na_2SO_4$, evaporated under $N_2$ and dried in vacuo at room-temperature to give 3.0 mg of the crude title compound (I1) as a pale-pink residue (3.0 mg, 10% crude yield); HRMS calcd for $C_{17}H_{18}N_3O_2$ (M+H$^+$) 296.13990, obsd 296.13733 (100%); $^1$H NMR (300 MHz, DMSO-d$_6$) δ 4.719 (s, 4H), 7.274-7.304 (m, 10H), 8.898 (s, 2H), ~11.7 (br s, 1H).

Example 2

Compound I2

Compound I2 can be represented by Formula V as follows:

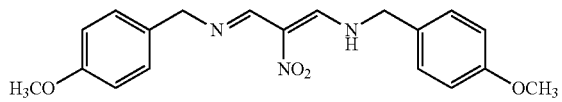

Formula V for Compound I2

Synthesis of (3E)-N-((E)-3-(4-methoxybenzylimino)-2-nitropropylidene)(4-methoxyphenyl)methanamine (I2)

A yellow-orange suspension of sodium nitromalonaldehyde monohydrate (15.7 mg, 0.10 mmol) in methanol (275 uL) and water (25 uL) was added dropwise over a 2 min period to a solution of 4-methoxybenzylamine in methanol (165 uL), water (15 uL) and 96% formic acid (0.83 uL, 0.022 mmol) and was stirred at room-temperature for 24 h. It was noted that during the NMA addition a precipitate started to crystallize out, and was analyzed and found to be the crude title compound (I2). Filtration gave a pale-yellow powder (14.5 mg, 41% crude yield) that was recrystallized from a minimum volume of absolute ethanol (~0.75 mL) yielding 13 mg (37%) of the title compound as pale-yellow, microcrystalline flakes: mp 131.5-132° C.; HRMS calcd for $C_{19}H_{22}N_3O_4$ (M+H$^+$) 356.1610, obsd 356.15571; $^1$H NMR (300 MHz, DMSO-d$_6$) δ 3.737 (s, 6H), 4.621 (s, 4H), 6.891, 6.885, 6.869, 6.862 (dd, 4H), 7.196-7.167 (d, 4H), 8.840 (s, 2H), ~11.7 (br s, 1H); $^{13}$C NMR (75 MHz, DMSO-d$_6$) δ 145.704, 135.410, 135.380, 128.787, 128.382, 128.199, 127.879, 127.230, 120.561, 64.383, 57.309, 52.166; Anal. Calcd for $C_{19}H_{21}N_3O_4$ (355.39): C, 64.21; H, 5.96; N, 11.82. Found: C, 64.04; H, 5.96; N, 11.86.

Example 3

Compound BC1

Compound BC1 can be represented by Formula VI as follows:

Formula VI for Compound BC!

As depicted, "Bn" is an unsubstituted benzyl moiety.

Synthesis of 2,6,9-Tribenzyl-4,8-dinitro-2,6,9-triazabicyclo[3.3.1]nona-3,7-diene (BC1)

A yellow-orange suspension of sodium nitromalonaldehyde monohydrate (63 mg, 0.40 mmol) in methanol (760 uL), water (32 uL) and 96% formic acid (3.2 uL, 0.084 mmol) was stirred at room-temperature and benzylamine (91.7 uL, 0.84 mmol) was added dropwise over a 5 min period during which the reaction solids dissolved, subsequently the crude product then quickly crystallized. The orange reaction mixture was stirred about 2 days at room-temperature. Filtration gave a yellow powder (63 mg) of which 59 mg was recrystallized from absolute ethanol (~10 mL) yielding 25 mg (26%) of the title compound BC1 as a yellow, microcrystalline solid: mp 184-185° C.; HRMS calcd for $C_{27}H_{26}N_5O_4$ (M+H$^+$) 484.1985, obsd 484.18924; $^1$H NMR (300 MHz, DMSO-d$_6$) δ 3.004 (s, 2H), 4.789-5.002 (q, 4H), 5.350 (s, 2H), 6.631-6.659 (d, 2H), 7.035-7.136 (m, 3H), 7.36-7.37 (br s, 10H), 8.800 (s, 2H); $^1$H NMR (300 MHz, CDCl$_3$) δ 2.948, 2.955 (d, 2H), 4.581, 4.630 (d, 2H), 4.974, 5.023 (d, 2H), 5.308 (s, 2H), 6.714, 6.737 (d, 2H), 7.090, 7.116, 7.170-7.20 (m, 3H), 7.289, 7.298, 7.310, 7.321, 7.335, 7.342, 7.353, 7.363, 7.375 (complex m, 10H), 8.358 (s, 2H); $^{13}$C NMR (75 MHz, DMSO-d$_6$) δ 145.704, 135.410, 135.380, 128.787, 128.382, 128.199, 127.879, 127.230, 120.561, 64.383, 57.309, 52.166; Anal. Calcd for $C_{27}H_{25}N_5O_4$ (483.52): C, 67.07; H, 5.21; N, 14.48. Found: C, 66.80; H, 5.13; N, 14.45.

Example 4

Compound BC6

Compound BC6 can be represented by Formula VII as follows:

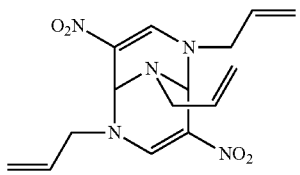

Formula VII of Compound BC6

Synthesis of 2,6,9-Triallyl-4,8-dinitro-2,6,9-triaza-bicyclo[3.3.1]nona-3,7-diene (BC6)

A yellow-orange suspension of sodium nitromalonaldehyde monohydrate (63.5 mg, 0.404 mmol) in 8.3% aq. methanol (1:11 v/v) solution (1200 uL), was mixed with a solution of 96% formic acid (3.9 uL, 0.100 mmol) in 8.3% aq. methanol solution (720 uL), and was stirred for several minutes at room-temperature. Allylamine (76 uL, 1.00 mmol) was added dropwise (~10 drops) over a ~20 sec period during which the reaction solids dissolved. The crude reaction mixture was stirred at room-temperature overnight. TLC (EtOAc: hexane {1:2 v/v}) showed a yellow, major spot for desired product at $R_f$=0.30 (UV) with at least two other minor spots at $R_f$=0.37 and 0.24 (UV). Reaction solvent and volatiles were evaporated in vacuo at 30° C. to give an orange-red semi-solid that was partitioned between EtOAc and water rendered alkaline with a minimum amount of satd. NaHCO$_3$. The aqueous layer was separated, extracted with EtOAc (3×), the combined organics were dried over Na$_2$SO$_4$ and concentrated in vacuo giving a dark red oil (41 mg). Flash chromatography on silica and elution with 0-0.5% MeOH:CH$_2$Cl$_2$ gave three components that were isolated and characterized. After evaporation of selected fractions, a yellow oil (14 mg, 21% yield) was confirmed as the major component by weight, and identified as desired product BC6 having spectra consistent with structure, confirmed by HRMS (DART_Pos) analysis which detected the product ion (M+H$^+$) 334.12210 (A ~23K) and NMR (300 MHz, CDCl$_3$ nt=16) δ 8.208 (s, 2H), 5.89-5.74 (m, 3H), 5.491-5.205 (m, 8H), 4.475, 4.450, 4.425, 4.400 (dd, 2H), 4.166, 4.162, 4.149, 4.145, 4.116, 4.112, 4.103, 4.098, dd, dd, 2H), 3.058, 3.038, 3.034, 3.012, 3.009, 2.993, 2.989, 2.946, 2.943, 2.924, 2.901, 2.879 (ddq, 2H). $^1$H NMR {of a prior preparative TLC (EtOAc:hexane {1:2 v/v}) purified sample, pumped in vacuo at 65° C. to give 0.4 mg} (300 MHz, DMSO-d$_6$ nt=512) δ 8.495 (s, 2H), 6.0-5.8 (m, 4H), 5.8-5.7 (m, 1H), 5.432, 5.392, 5.387, 5.335, 5.330, 5.307, 5.303, 5.273, 5.269, 5.182 (dd, dd, dd, dd, 8H), 4.339, 4.321, 4.298 (dt, 4H); $^{13}$C NMR {of the flash chromatographed pure sample, ~14 mg} (75 MHz, CDCl$_3$ nt=30720) δ 144.387, 132.334, 131.495, 121.581, 121.483, 120.701, 65.819, 57.541, 52.798; HRMS (DART, flash purified sample) calcd for $C_{15}H_{20}N_5O_4$ (M+H$^+$) 334.1515, obsd 334.12210.

Example 5

Compound TC1

A tricyclic compound is synthesized from BC1 using known organic synthesis techniques. Compound TC1 can be represented by Formula VII as follows, where "Bn" represents an unsubstituted benzyl moiety:

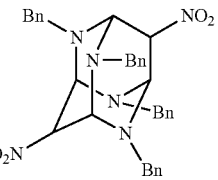

Formula VII for Compound TC1

Synthesis of 2,6-Dinitro-4,8,9,10-tetraaza-4,8,9,10-tetrabenzyladamantane (TC1)

A suspension of 2,6,9-tribenzyl-4,8-dinitro-2,6,9-triaza-bicyclo[3.3.1]nona-3,7-diene (BC1) (8.0 mg, 0.0166 mmol) in 4% aq. CH$_3$CN (500 uL) was treated with 91% formic acid (1.0 uL, 0.024 mmol) catalyst, and benzylamine (~2.2 uL, 0.020 mmol) was added at room-temperature. The reaction mixture was immersed in a hot (81° C.) oil bath and soon changed to a solution, and was heated for 2.5 h. Analysis of the crude reaction mixture by HRMS detected the intended product ion (M+H$^+$) 591.30675 (A ~2.3K); calcd for $C_{34}H_{35}N_6O_4$ (M+H$^+$) 591.27198. Expansion showed an ion (M+1)H$^+$592.34379 and ion (M+2)H$^+$593.36871. The major component of the reaction products mixture was unreacted BC1 which was confirmed by HRMS, calcd for $C_{27}H_{26}N_5O_4$ (M+H$^+$) 484.1985, obsd 484.19637 (A ~72K); and $^1$H NMR (300 MHz, DMSO-d$_6$) was consistent with structure for BC1 (25H).

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A bicyclic intermediate compound having a structure of Formula II:

wherein R is one of a benzyl, 4-methoxybenzyl, acetyl, nitro, formyl, allyl and a carboethoxyl group.

2. The bicyclic intermediate compound according to claim 1, wherein the bicyclic intermediate compound is a 2,6,9-tribenzyl-4,8-dinitro-2,6,9-triazabicyclo[3.3.1]nona-3,7-diene, or a pharmaceutically acceptable salt or solvate thereof.

3. The bicyclic intermediate compound according to claim 1, wherein the bicyclic intermediate compound is a 2,6,9-tri(4-methoxybenzyl)-4,8-dinitro-2,6,9-triazabicyclo[3.3.1]nona-3,7-diene, or a pharmaceutically acceptable salt or solvate thereof.

4. The bicyclic intermediate compound according to claim 1, wherein the bicyclic intermediate compound is a 2,6,9-triacetyl-4,8-dinitro-2,6,9-triazabicyclo[3.3.1]nona-3,7-diene, or a pharmaceutically acceptable salt or solvate thereof.

5. The bicyclic intermediate compound according to claim 1, wherein the bicyclic intermediate compound is a 2,4,6,8,9-pentanitro-2,6,9-triazabicyclo[3.3.1]nona-3,7-diene, or a pharmaceutically acceptable salt or solvate thereof.

6. The bicyclic intermediate compound according to claim 1, wherein the bicyclic intermediate compound is a 2,6,9-triformyl-4,8-dinitro-2,6,9-triazabicyclo[3.3.1]nona-3,7-diene, or a pharmaceutically acceptable salt or solvate thereof.

7. The bicyclic intermediate compound according to claim 1, wherein the bicyclic intermediate compound is a 2,6,9-triallyl-4,8-dinitro-2,6,9-triazabicyclo[3.3.1]nona-3,7-diene, or a pharmaceutically acceptable salt or solvate thereof.

8. The bicyclic intermediate compound according to claim 1, wherein the bicyclic intermediate compound is a 2,6,9-tricarboethoxyl-4,8-dinitro-2,6,9-triazabicyclo[3.3.1]nona-3,7-diene, or a pharmaceutically acceptable salt or solvate thereof.

9. A method for preparing a bicyclic intermediate compound of claim 1, comprising reacting sodium nitromalonaldehyde monohydrate with a substituted amine, wherein the substituted amine is benzyl, 4-methoxybenzyl, acetyl, nitro, formyl, allyl or a carboethoxyl substituted amine, for forming at least one bicyclic intermediate of claim 1.

10. The method according to claim 9, wherein the substituted amine is acetyl, nitro, formyl or a carboethoxyl substituted amine.

11. The method according to claim 9, wherein the substituted amine is one of allylamine, benzyl- or 4-methoxybenzylamine.

12. A method for preparing a bicyclic intermediate compound of claim 1, comprising reacting an acyclic intermediate compound having a structure of Formula 1:

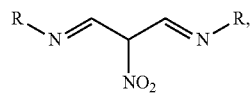

where R is as defined in claim 1, with a substituted amine, wherein the substituted amine is benzyl, 4-methoxybenzyl, acetyl, nitro, formyl, allyl or a carboethoxyl substituted amine, for forming at least one bicyclic intermediate compound of claim 1.

13. The method according to claim 12, wherein the substituted amine is acetyl, nitro, formyl or a carboethoxyl substituted amine.

14. The method according to claim 12, wherein the substituted amine is one of allylamine, benzyl- or 4-methoxybenzylamine.

* * * * *